United States Patent [19]

Mouwen et al.

[11] 4,056,476

[45] Nov. 1, 1977

[54] BLOOD FILTER MEDIA

[75] Inventors: Herman Charles Mouwen, Ventura, Calif.; William Lauer, Madison; Steven Louis Weinberg, East Brunswick, both of N.J.

[73] Assignees: Johnson & Johnson, New Brunswick, N.J.; Purolator, Inc., Del.

[21] Appl. No.: 696,256

[22] Filed: Sept. 2, 1976

Related U.S. Application Data

[63] Continuation-in-part of Ser. No. 553,703, Feb. 27, 1975, abandoned.

[51] Int. Cl.² .......................................... B01D 25/06
[52] U.S. Cl. ............................. 210/446; 139/383 B; 139/425 A; 162/DIG. 1; 210/DIG. 23; 210/460; 210/507

[58] Field of Search .............. 210/448, 500, 507, 508, 210/DIG. 23, 446, 460; 162/DIG. 1, 348; 139/383, 425.5

[56] References Cited

U.S. PATENT DOCUMENTS

| 2,551,175 | 5/1951 | Smith | 162/DIG. 1 |
| 3,132,099 | 5/1964 | Eilhaver | 210/507 |
| 3,593,854 | 7/1971 | Swank | 210/DIG. 23 |
| 3,603,354 | 9/1971 | Lee et al. | 139/383 |
| 3,765,536 | 10/1973 | Rosenberg | 210/507 |
| 3,851,681 | 12/1974 | Egan | 162/DIG. 1 |
| 3,870,639 | 3/1975 | Moore et al. | 210/DIG. 23 |

Primary Examiner—Theodore A. Granger

[57] ABSTRACT

An improved blood filter media comprising a woven fabric having a pore size distribution rating of 20 microns and being woven with monofilament yarns in a regular, even-sided twill weave.

2 Claims, 2 Drawing Figures

BLOOD FILTER MEDIA

This is a continuation-in-part application of our copending application, Ser. No. 553,703, filed Feb. 27, 1975, now abandoned.

This invention relates to an improved blood filter media.

BACKGROUND OF THE INVENTION

The filtration of blood is a delicate and critical operation. Blood filtration requires that the debris, such as clots and various types of agglomerates, be removed without removing desirable red cells or other desirable portions of the blood and without degradation of the blood.

Whole blood comprises plasma, red cells, white cells and platelets. The red cells have diameters of from about 8 to 10 microns and the white blood cells have diameters of from about 12 to 20 microns. Whole blood, after storage for a relatively short period of time, and blood which is passing through an extracorporeal circuit, such as is used in open heart surgery, or through a dialysis operation will tend to degrade and build debris in the blood. This debris must be filtered from the blood before the blood is returned or given to a patient. The debris may comprise blood clots or various types of aggregates of the platelet type or the leucocyte type and may include agglomeration of protein precipitates and other undesirable debris. In filtering this blood, the ultimate is to remove all of the undesirable debris while not removing any of the desirable red blood cells or white blood cells or the platelets. Hence, media used in the filtration of blood must meet certain requirements. It must have no harmful effects on the blood or degrade the blood. The media should be stable during filtration, that is its pore size distribution range should not be altered. Very often some media will start to plug and after limited use will remove some of the desirable red and white blood cells from the blood. The media should have as much open area as possible to make the most efficient use of the media area and make the filter small and easily handled.

More specifically media used in filtering blood should have a relatively uniform pore size and the media should maintain this pore size throughout the use of the media. In prior art blood filtration medias made from woven fabrics, one technique for accomplishing this is to bond the woven yarns at their cross-over point. This means a binder material must be added to the media and the exact same amount added at each cross-over point. If too much binder is added at a cross-over the pore size is decreased and the pore size distribution range increased upsetting the very delicate balance required in filtering blood. Another technique for obtaining the desired stability in a woven fabric blood filter media is to calender the fabric. This process tends to flatten the yarns at their cross-over point and also disrupts the pore size rating of the media.

Furthermore, the larger the yarns used in producing the filter fabric the more stable it may be made by utilizing the friction of the crossing yarns. However, the larger the yarns the less the open area and the greater the pressure drop across the media which is undesirable when filtering blood.

SUMMARY OF THE PRESENT INVENTION

We have discovered an improved blood filter media. Our improved media has a nominal pore size rating of 20 microns. Our improved media is stable during use and retains this pore size rating even after considerable quantities of blood have been filtered. Our improved filter media has minimal deleterious effects on the blood being filtered. Unexpectedly, our new blood filter media has a very narrow distribution range and while it removes all of the undesirable debris from the blood it does not remove the desirable red blood cells and white blood cells in the blood.

In accordance with the present invention, our improved blood filter media is a woven fabric. The fabric is woven in a regular, even-sided two up and two down twill weave using monofilament yarns having a yarn diameter of 30 to 36 microns. The woven fabric has a nominal pore size rating of 20 microns and a distribution range of from 17 microns to 23 microns. Preferably our improved blood filter media is woven with nylon monofilament yarns having a diameter of 32 microns.

What we have discovered is that if a fabric is woven using 30 to 36 micron diameter monofilament yarns in a regular, even-sided, two up and two down weave to produce a nominal 20 micron pore size rating you unexpectedly obtain a very narrow pore size distribution range of 6 microns and perhaps more unexpectedly are able to maintain both the nominal pore size and the narrow distribution range throughout extended use of the filter media. Furthermore, these unexpected results are obtained without calendering or bonding the fabric, which it is believed would in fact tend to disrupt these desired results.

BRIEF DESCRIPTION OF THE DRAWINGS

The invention will be further described in conjunction with the accompanying drawings wherein.

DETAILED DESCRIPTION OF THE DRAWINGS

Figure 1:
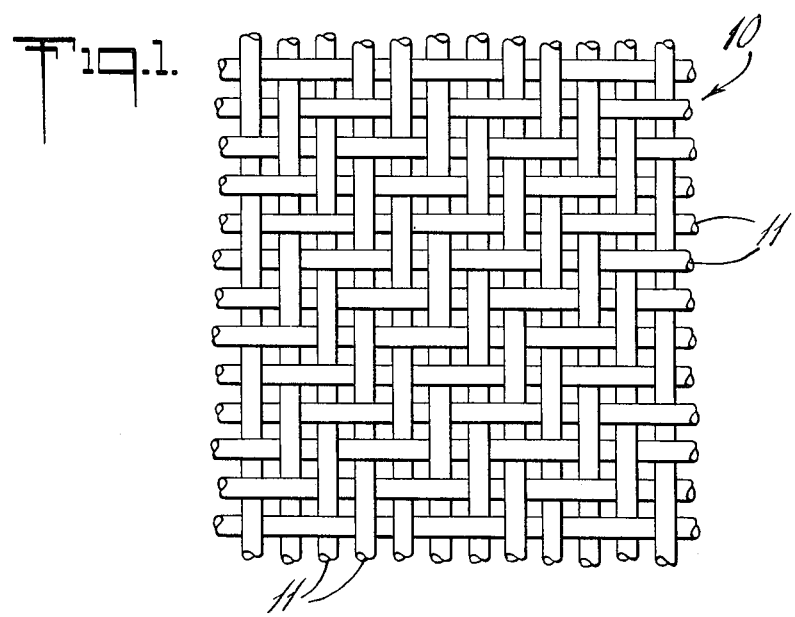
FIG. 1 is a plan view of the improved filter media of the present invention.

Referring to the drawings, in FIG. 1, there is shown the improved blood filter media 10 of the present invention. The media is woven with nylon monofilament yarns 11 and these yarns are used in both the warp and the filling directions. The media is woven in a regular, even-sided, two up and two down twill weave. Though nylon monofilament yarns are preferred, the media may also be woven with polyester monofilament yarns or other monofilament yarns which will not degrade or have a deleterious effect on the blood. It is important that monofilament yarns be used as it is believed that such yarns, being smoother and with less rough areas such as are present in multifilament or spun yarns, have a longer life and have less deleterious effects on the blood. The size of the monofilaments should be as small as possible. The smaller the diameter of each yarn, the more open area in the filter while still maintaining a desired pore size. Sizes of from about 30 microns in diameter to 36 microns in diameter have been found suitable in accordance with the present invention.

The media should not be calendered or the yarns bonded or held together at their cross-over points. This is important as it appears that calendering or bonding tends to disrupt the pore size rating and distribution range and, surprisingly, does not have any improved effect on the stability of the two up and two down twill weave. By stability, it is meant that its initially rated pore size is maintained throughout its expected life. The improved blood filter media has a nominal pore size rating of 20 microns. If its rating is less than 20 microns, it will remove desirable portions such as white and red blood cells from the blood being filtered. If its pore size rating is greater than 20 microns, it will not remove all of the undesirable debris. The media should have a particle distribution range of from 17 microns to 23 microns. This is a narrow distribution range; however, it is important to the present invention. A wider distribution range will either remove too many important portions of the blood or not remove sufficient debris or, in some instances, may have both harmful effects. Furthermore, the wider distribution ranges do not maintain that distribution range during extended uses and hence are unsatisfactory.

The two up and two down twill weave using substantially the same size yarns in the warp and fill direction produces a fabric having very uniform openings which is essential to the present invention. The fact that our fabric media is not calendered or heat set allows us to insure the maintenance of this opening in a blood filter unit.

It has been theorized that the above-described twill weave combined with the lack of calendering produces some depth to the fabric media or depth to the openings or pores in the fabric. This slight depth to the pore helps in preventing slightly larger particles than the size of the opening from changing shape and squeezing through an opening or pore.

Figure 2:
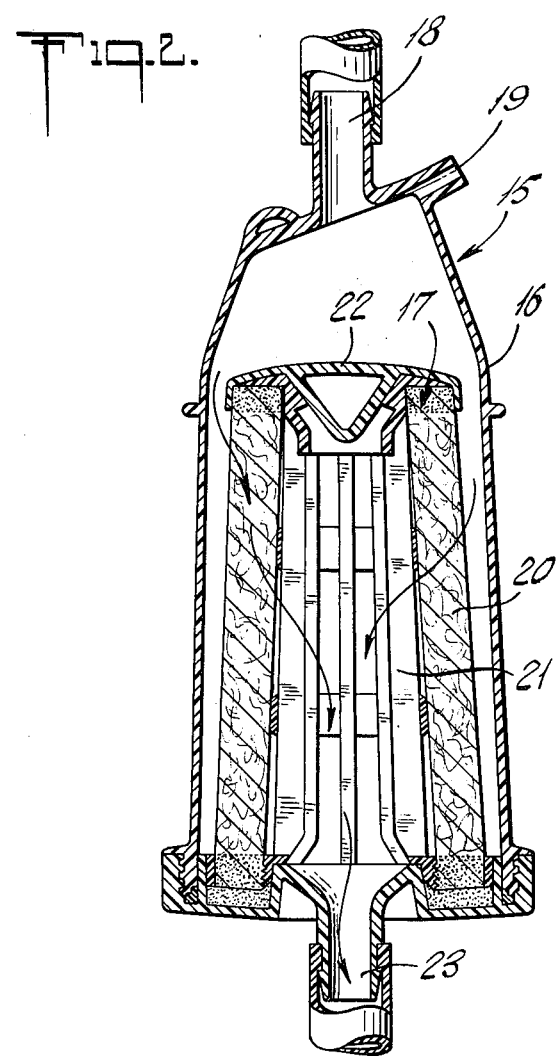
FIG. 2 is a cross-sectional view of a blood filter unit incorporating the media of the present invention.

In FIG. 2, there is shown one embodiment of a blood filter unit 15 that utilizes the blood filter media of the present invention. The unit comprises a housing 16 and a filter cartridge 17 disposed within the housing. At the top of the housing is an inlet opening 18 for the incoming blood and an air vent 19 to allow air to escape from the filter unit. The filter cartridge is cylindrical in shape. The outside walls of the cylinder are formed by the filter media 20 of the present invention. The media may be flat or fluted in its cylindrical form. The inside surface of the media is supported by an open mesh-like cylinder 21. The upper end of the media is sealed by a cap 22. The lower end of the media is sealed into the bottom portion of the housing. In the center of the bottom portion of the housing and positioned adjacent the center of the filter cartridge is the blood outlet opening 23.

In operation, the blood flows in the path as shown by the arrows in the drawing. The blood enters through the inlet 18 and from outside the filter cartridge into the center of the cartridge and out the outlet 23.

Though a cylindrical blood filter unit has been shown, the unit may be of any desired shape and the media may take any configuration as desired.

Having thus described the present invention, it should be understood that many variations and modifications may be made without departing from the scope of the invention itself; the invention is only limited by the scope of the claims appended hereto.

What is claimed is:

1. In a unit for filtering blood, the improvement comprising an uncalendered, unbonded, woven fabric filter media having a nominal pore size rating of 20 microns, a pore size distribution range of from 17 microns to 23 microns, and woven with monofilament yarns having a yarn diameter of from 30 microns to 36 microns, said media being woven in a two-up and two-down twill weave, whereby the media is stable and retains its nominal pore size rating and pore size distribution range during use.

2. A woven fabric filter media according to claim 1 wherein the monofilament yarns are nylon monofilament yarns having a yarn diameter of 32 microns.

* * * * *